United States Patent [19]

Allgeier

[11] Patent Number: 4,851,424
[45] Date of Patent: Jul. 25, 1989

[54] 1-PHENYL-LOWER ALKYL-IMIDAZOLE 4- OR 5-CARBOXAMIDE COMPOUNDS WHICH ARE USEFUL IN THE TREATMENT OF EPILEPSY

[75] Inventor: Hans Allgeier, Lörrach-Haagen, Fed. Rep. of Germany

[73] Assignee: Ciba-Geigy Corporation, Hawthorne, N.Y.

[21] Appl. No.: 53,913

[22] Filed: May 26, 1987

[30] Foreign Application Priority Data

Jun. 6, 1986 [CH] Switzerland .................. 2294/86
Oct. 9, 1986 [CH] Switzerland .................. 4034/86

[51] Int. Cl.$^4$ .................. C07D 233/70; A61K 31/415
[52] U.S. Cl. .................. 514/400; 548/343
[58] Field of Search .................. 548/343; 514/400

[56] References Cited

U.S. PATENT DOCUMENTS

| | | | |
|---|---|---|---|
| 2,897,205 | 7/1959 | Leanza | 548/343 |
| 3,691,178 | 9/1972 | Baldwin et al. | 548/343 |
| 3,991,072 | 11/1976 | Roevens et al. | 548/343 |
| 4,185,992 | 1/1980 | Gilnour | 71/92 |
| 4,346,097 | 8/1982 | Schweiss et al. | 548/362 |

FOREIGN PATENT DOCUMENTS 0028833 5/1981 European Pat. Off. ............ 548/343

OTHER PUBLICATIONS

Derwent Abstr. 84-272807/44 of Japanese 84/167515A, (9/84).
CA 102:56152t (1985).
CA 94:30642u (1981).
Derwent Abstract 72139x/39 of Belgium 839120 (9/76).

Primary Examiner—Mary C. Lee
Assistant Examiner—Zinna Northington
Attorney, Agent, or Firm—JoAnn Villamizar; Irving M. Fishman

[57] ABSTRACT

1-Phenyl-lower alkylimidazole-4- and/or 5-carboxamides of the formula

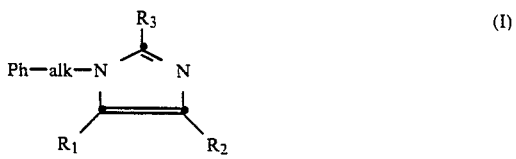

(I)

in which Ph represents phenyl substituted by lower alkyl and/or by halogen, alk represents lower alkylidene, one of the radicals $R_1$ and $R_2$ is carbamoyl optionally substituted by lower alkyl or by lower alkanoyl and the other is hydrogen, lower alkyl, or carbamoyl optionally substituted by lower alkyl or by lower alkanoyl, and $R_3$ represents hydrogen or lower alkyl, have anticonvulsive properties and can be used as anticonvulsives. They are manufactured as follows: in a compound of the formula

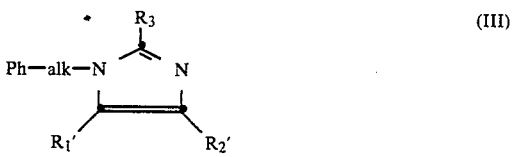

(III)

in which $R_1'$ represents a radical $R_1$ or X and $R_2'$ represents a radical X, or $R_1'$ represents a radical X and $R_2'$ represents a radical $R_2$, where X represents a group that can be converted into carbamoyl that optionally is mono- or di-substituted by lower alkyl or monosubstituted by lower alkanoyl, the radical X or the radicals X is/are converted into carbamoyl that optionally is mono- or di-substituted by lower alkyl or monosubstituted by lower alkanoyl.

13 Claims, No Drawings

1-PHENYL-LOWER ALKYL-IMIDAZOLE 4- OR 5-CARBOXAMIDE COMPOUNDS WHICH ARE USEFUL IN THE TREATMENT OF EPILEPSY

The invention relates to novel aralkylimidazole derivatives, especially 1-phenyl-lower alkylimidazole-4- and/or -5-carboxamides of the formula

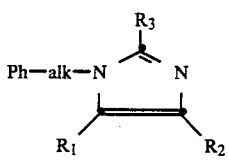

in which Ph represents phenyl substituted by lower alkyl and/or by halogen, alk represents lower alkylidene, one of the radicals $R_1$ and $R_2$ is carbamoyl optionally substituted by lower alkyl or by lower alkanoyl and the other is hydrogen, lower alkyl, or carbamoyl optionally substituted by lower alkyl or by lower alkanoyl, and $R_3$ represents hydrogen or lower alkyl, for use in a method for the therapeutic treatment of the human or animal body, to pharmaceutical preparations containing them and to their use as the active ingredients of medicaments and to the compounds themselves, with the proviso that, in compounds of the formula I in which $R_1$ and $R_2$ are the same and each represents carbamoyl or N-methylcarbamoyl, if $R_3$ represents hydrogen at least one substituent of Ph is bonded in the o-position, and to processes for their manufacture.

The phenyl radical Ph contains, for example, up to and including 3, especially 1 or 2, of the mentioned substituents, preferably one lower alkyl or halogen substituent or one or two halogen substituents, or one lower alkyl and one halogen substituent, preferably at least one of the mentioned substituents being bonded in an o-position. As examples there may be mentioned: o-halophenyl, 2,6- and also 2,5-, 2,3- and 2,4-dihalophenyl, and also o-lower alkylphenyl, especially 2,6-difluorophenyl.

Optionally lower alkyl- or lower alkanoyl-substituted carbamoyl $R_2$ and, where appropriate, $R_1$ is, for example, carbamoyl or N-lower alkyl-, N,N-di-lower alkyl- or, secondly, N-lower alkanoyl-carbamoyl.

Hereinbefore and hereinafter there are to be understood by "lower" organic groups and compounds preferably those groups and compounds that contain up to and including 7, especially up to and including 4, carbon atoms (C atoms).

Lower alkyl is, for example, $C_1-C_4$-alkyl, such as methyl, ethyl, propyl, isopropyl, butyl, and also secondary butyl, isobutyl or tertiary butyl, but may also be a $C_5-C_7$-alkyl group, such as a pentyl, hexyl or heptyl group.

Halogen is, for example, halogen having an atomic number of up to and including 35, such as fluorine, chlorine or, secondly, bromine.

Lower alkylidene is, for example, $C_1-C_4$-alkylidene, especially 1,1-$C_1-C_4$-alkylidene, such as methylene, and also ethylidene, 1,1-propylidene or 1,1-butylidene, but may also be 2,2-$C_3-C_4$-alkylidene, such as 2,2-propylidene (isopropylidene) or 2,2-butylidene.

N-lower alkylcarbamoyl is, for example, N-$C_1-C_7$-alkylcarbamoyl, especially N-$C_1-C_4$-alkylcarbamoyl, such as methyl- or ethylcarbamoyl.

N,N-di-lower alkylcarbamoyl is, for example, N,N-di-$C_1-C_4$-alkylcarbamoyl, such as dimethylcarbamoyl, and also diethyl- or di-n-propyl-carbamoyl.

N-lower alkanoylcarbamoyl is, for example, N-$C_2-C_7$-alkanoylcarbamoyl, especially N-$C_2-C_4$-alkanoylcarbamoyl, such as acetyl-, propionyl- or butyryl-carbamoyl, but may also be formylcarbamoyl or N-$C_5-C_7$-alkanoylcarbamoyl, such as pivaloylcarbamoyl.

The compounds of the formula I have valuable pharmacological properties, especially a pronounced anticonvulsive activity which can be demonstrated, for example, in mice on the basis of a distinct metrazole antagonism in a dosage range of approximately 10 mg/kg and above p.o. and in mice and rats on the basis of a marked protective action against convulsions triggered by electric shock in a dosage range of approximately 3.5 mg/kg and above p.o.. The compounds of the formula I are accordingly excellently suitable for the treatment of convulsions of various origins, for example for the treatment of epilepsy. They can accordingly be used as anticonvulsive, for example antiepileptic, active ingredients in medicaments.

The invention relates especially to compounds of the formula I in which Ph represents phenyl that is mono-, di- or tri-substituted by lower alkyl and/or by halogen, alk represents lower alkylidene, one of the radicals $R_1$ and $R_2$ is carbamoyl, N-lower alkylcarbamoyl, N,N-di-lower alkylcarbamoyl or N-lower alkanoylcarbamoyl and the other is hydrogen, lower alkyl, carbamoyl, N-lower alkylcarbamoyl, N,N-di-lower alkylcarbamoyl or N-lower alkanoylcarbamoyl, and $R_3$ represents hydrogen or lower alkyl, for use in a method for the therapeutic treatment of the human or animal body, and also to the above-defined compounds themselves, with the proviso that, in compounds of the formula I in which $R_1$ and $R_2$ are the same and each represents carbamoyl or N-methylcarbamoyl, if $R_3$ represents hydrogen at least one substituent of Ph is bonded in the o-position, and preferably to those in which at least one of the mentioned substituents of Ph is bonded in the o-position and/or alk represents methylene, $R_1$ represents hydrogen or carbamoyl and $R_2$ represents carbamoyl.

The invention relates more especially to compounds of the formula I in which Ph represents phenyl that is monosubstituted by $C_1-C_4$-alkyl or disubstituted by halogen or by halogen and $C_1-C_4$-alkyl, wherein $C_1-C_4$-alkyl is, for example, methyl and halogen has an atomic number of up to and including 35 and is, for example, fluorine or, secondly, chlorine, alk represents 1,1- or 2,2-$C_1-C_4$-alkylidene, such as methylene or ethylidene, one of the radicals $R_1$ and $R_2$ is carbamoyl, N-$C_1-C_4$-alkyl- or N,N-di-$C_1-C_4$-alkyl-carbamoyl, such as methyl- or dimethylcarbamoyl, or N-$C_2-C_7$-alkanoylcarbamoyl, such as acetyl- or pivaloyl-carbamoyl, and the other is hydrogen, carbamoyl, N-$C_1-C_4$-alkyl- or N,N,-di-$C_1-C_4$-alkyl-carbamoyl, such as methyl- or dimethylcarbamoyl, or N-$C_2-C_7$-alkanoylcarbamoyl, such as acetyl- or pivaloyl-carbamoyl, and $R_3$ represents hydrogen or, secondly, $C_1-C_4$-alkyl, such as methyl, for use in a method for the therapeutic treatment of the human or animal body, and also to the above-defined compounds themselves, with the proviso that, in compounds of the formula I in which $R_1$ and $R_2$ are the same and each represents carbamoyl or N-methylcarbamoyl, if $R_3$ represents hydrogen at least one substituent of Ph is bonded in the o-position, and preferably to those in which at least one of the mentioned substituents of Ph is bonded in the o-position and/or alk represents methylene, $R_1$ represents hydrogen or carbamoyl and $R_2$ represents carbamoyl.

The invention preferably relates to compounds of the formula I in which Ph represents o-$C_1$-$C_4$-alkylphenyl, o-halophenyl or 2,6- or 2,5-di-halophenyl, wherein $C_1$-$C_4$-alkyl is, for example, methyl and halogen has an atomic number of up to and including 35 and, independently of any other, is, for example, fluorine or, secondly, chlorine or bromine, alk represents 1,1-$C_1$-$C_4$-alkylidene, such as methylene, one of the radicals $R_1$ and $R_2$ is carbamoyl, N-$C_1$-$C_4$-alkylcarbamoyl, such as methylcarbamoyl, N,N-di-$C_1$-$C_4$-alkylcarbamoyl, such as dimethylcarbamoyl, or N-$C_2$-$C_7$-alkanoylcarbamoyl, such as acetylcarbamoyl, and the other is hydrogen, carbamoyl, N-$C_1$-$C_4$-alkylcarbamoyl, such as methyl- or ethyl-carbamoyl, N,N-di-$C_1$-$C_4$-alkylcarbamoyl, such as dimethylcarbamoyl, or N-$C_2$-$C_4$-alkanoylcarbamoyl, such as acetylcarbamoyl, and $R_3$ represents hydrogen, and preferably relates to those in which alk represents methylene, $R_1$ represents hydrogen or carbamoyl and $R_2$ represents carbamoyl, and very especially to those in which alk represents methylene, $R_1$ represents hydrogen and $R_2$ represents carbamoyl.

The invention relates especially, on the one hand, to compounds of the formula I in which Ph represents o-$C_1$-$C_4$-alkylphenyl, such as o-methylphenyl, o-halophenyl, such as o-chloro- or o-fluorophenyl, or 2,6-dihalophenyl, such as 2,6-difluorophenyl, alk represents methylene, $R_1$ represents hydrogen, $R_2$ represents carbamoyl, N-$C_1$-$C_4$-alkylcarbamoyl, such as N-methylcarbamoyl, N,N-di-$C_1$-$C_4$-alkylcarbamoyl, such as N,N-dimethylcarbamoyl, or N-$C_2$-$C_4$-alkanoylcarbamoyl, such as N-acetylcarbamoyl, and $R_3$ represents hydrogen, and preferably relates to those in which $R_2$ represents carbamoyl.

The invention relates especially, on the other hand, to compounds of the formula I in which Ph represents 2,6-dihalophenyl, such as 2,6-difluorophenyl, alk represents methylene, $R_1$ represents carbamoyl, N-$C_1$-$C_4$-alkylcarbamoyl, such as N-methylcarbamoyl, N,N-di-$C_1$-$C_4$-alkylcarbamoyl, such as N,N-dimethylcarbamoyl, or, secondly, N-$C_2$-$C_4$-alkanoylcarbamoyl, such as N-acetylcarbamoyl, $R_2$ represents hydrogen, $C_1$-$C_4$-alkyl, such as methyl, or carbamoyl, or represents N-$C_1$-$C_4$-alkylcarbamoyl, such as N-methylcarbamoyl, N,N-di-$C_1$-$C_4$alkylcarbamoyl, such as N,N-dimethylcarbamoyl, or, secondly, N-$C_2$-$C_4$-alkanoylcarbamoyl, such as N-acetylcarbamoyl, each identical to $R_1$, and $R_3$ represents hydrogen, and preferably relates to those in which $R_1$ and $R_2$ represent carbamoyl.

The invention relates first and foremost to compounds of the formula I in which Ph represents o-$C_1$-$C_4$-alkylphenyl, such as o-methylphenyl, o-halophenyl, such as o-fluoro- or o-chlorophenyl, or 2,6-dihalophenyl, such as 2,6-difluorophenyl, and also 2,4-dihalophenyl, such as 2,4-difluorophenyl, or 2,5-dihalophenyl, such as 2,5-difluoro-or 2-fluoro-5-chlorophenyl, alk represents methylene, $R_1$ represents hydrogen, $R_2$ represents carbamoyl and $R_3$ represents hydrogen.

The invention preferably relates to the compounds of the formula I mentioned in the Examples.

The process according to the invention for the manufacture of the compounds of the formula I is based on methods known per se. It is characterised in that (a) the radical of the formula Ph-alk- is introduced into a compound of the formula

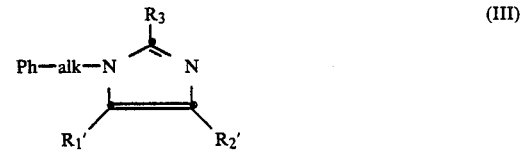

or into a salt thereof, or (b) in a compound of the formula

in which $R_1'$ represents a radical $R_1$ or X and $R_2'$ represents a radical X, or $R_1'$ represents a radical X and $R_2'$ represents a radical $R_2$, where X represents a group that can be converted into carbamoyl that optionally is mono- or di-substituted by lower alkyl or monosubstituted by lower alkanoyl, the radical X or the radicals X is/are converted into carbamoyl that optionally is mono- or di-substituted by lower alkyl or monosubstituted by lower alkanoyl, or (c) for the manufacture of compounds of the formula I in which $R_1$ represents hydrogen or lower alkyl, $R_2$ represents di-lower alkylated carbamoyl and $R_3$ represents hydrogen, a compound of the formula Ph—alk—$NH_2$ (IV)

is condensed with an isonitrile of the formula

in which $X_3$ represents a nucleofugal leaving group, and if desired, in each case, an isomeric mixture which may be obtained is separated into its components and the desired isomer is isolated, a compound obtained in accordance with the process is converted into a different compound of the formula I and/or a diastereoisomeric or enantiomeric mixture obtained in accordance with the process is separated into the diastereoisomers and/or enantiomers.

The reactions in accordance with the process and the manufacture of novel starting materials and intermediates are effected analogously to the manner in which known starting materials and intermediates are reacted and formed. The appropriate customary auxiliaries, such as catalysts, condensation and solvolysis agents and/or solvents or diluents, and reaction conditions, such as temperature and pressure conditions, and also, where appropriate, protective gases, are used, even if this is not expressly mentioned hereinafter.

The introduction of the radical of the formula Ph-alk- into compound II in accordance with process variant (a) is effected, for example, by reaction with a reactive ester of a corresponding phenyl-lower alkanol that is substituted in the phenyl moiety.

Reactive esters of phenyl-lower alkanols substituted in the phenyl moiety have, for example, the formula Ph—alk—$X_4$ (VI), there coming into consideration as reactive esterified hydroxy $X_4$ preferably hydroxy esterified by a mineral acid or an organic sulphonic acid, such as by a hydrohalic acid or an aliphatic or aromatic sulphonic acid, for example chlorine, bromine or iodine, or methane-, ethane-, benzene- or p-toluene-sulphonyloxy.

The reaction is carried out, for example, under basic conditions, such as in the presence of a basic condensation agent or by using the component II in the form of a salt, if necessary while heating, preferably in a solvent or diluent. Basic condensation agents are, for example, basic condensation agents that form salts with the component II, such as alkali metal alcoholates, for example sodium methoxide, potassium tertiary butoxide or sodium ethoxide, alkali metal or alkaline earth metal amides, for example sodium amide or lithium diisopropylamide. As mentioned, the conversion of the component II into one of its salts is advantageously effected beforehand, for example by reaction with one of the mentioned bases. Solvents for carrying out the reaction in the presence of an alcoholate are preferably the corresponding alcohols and, when the reaction is carried out in the presence of metal amides, they are, for example, aprotic organic solvents, such as N-lower alkylalkanoic acids amides, phosphoric acid lower alkylamides or di-lower alkyl sulphoxides, for example dimethylformamide, hexamethylphosphoric acid triamide or dimethyl sulphoxide. The reaction preferably takes place at elevated temperature, for example in a temperature range of approximately from 20° to 150° C., preferably of approximately from 25° to 100° C.

When starting from compounds II in which $R_1$ and $R_2$ are different, mixtures of the two possible isomers may be obtained, and these must be separated in order to isolate only one isomer.

The process is therefore suitable especially for the manufacture of compounds in which $R_1$ and $R_2$ represent identical, optionally mono- or di-lower alkylated carbamoyl groups.

Starting materials II can be manufactured, for example, as follows: in a compound of the formula

(VII)

in which one of the radicals $R_1'$ and $R_2'$ is a halocarbonyl or lower alkoxycarbonyl group and the other is hydrogen, lower alkyl or a halocarbonyl or lower alkoxycarbonyl group, the halocarbonyl or lower alkoxycarbonyl group(s) is/are converted into optionally mono- or di-lower alkylated carbamoyl by reaction with ammonia or with a mono- or di-lower alkylamine.

Compounds VII, in turn, can be manufactured by reacting imidazole-4,5-dicarboxylic acid with thionyl chloride, if necessary in the presence of catalytic amounts of dimethylformamide or pyridine, to form the 4,5-dicarboxylic acid chloride, or with a lower alkanol in the presence of catalytic amounts of mineral acids, for example hydrochloric acid or sulphuric acid, to form a 4,5-dicarboxylic acid lower alkyl ester. A general method of formation consists in reacting a compound of the formula Ph—C(=O)—R (VIII), in which R represents hydrogen or lower alkyl, in the presence of an acidic condensation agent, for example sulphuric acid in boiling ethanol or tetrahydrofuran, with a compound of the formula $H_2N-C(R_1')=C(R_2')-NH_2$ (IX), in which one of the radicals $R_1'$ and $R_2'$ is hydrogen, lower alkyl or cyano and the other is cyano, and in the reaction product of the formula $H_2N-C(R_1')=C(R_2')-N=C(R)-Ph$ (X) reducing the C-N double bond to the single bond, for example using sodium borohydride in methanol/tetrahydrofuran, and condensing the reaction product, for example in boiling diethylene glycol dimethyl ether, with formic acid or, in the presence of an acidic catalyst, with an orthoformic acid ester, for example at approximately from 80° to 100° C. with orthoformic acid triethyl ester, and converting the cyano group(s) into carbamoyl by means of basic hyrolysis or into N-lower alkyl- or N,N-di-lower alkylcarbamoyl by reaction with a lower alkanol under acidic conditions and then with a lower alkyl- or di-lower alkyl-amine and mild hydrolysis of the N-lower alkyl- or N,N-di-lower alkyl-amidine formed.

Groups X that can be converted into optionally mono- or di-lower alkylated or lower alkanoylated carbamoyl radicals in accordance with process variant (b) are, for example, carboxy groups that are free, esterified or in salt or anhydride form, the cyano group or optionally lower alkylated or lower alkanoylated amidino groups.

Esterified carboxy groups are, for example, carboxy groups esterified by a lower alkanol or a lower alkyl mercaptan, that is to say lower alkoxy- or lower alkylthio-carbonyl groups, but they may also be esterified by any other alcohol or mercaptan, for example by an optionally substituted phenol.

Carboxy groups in salt form are, for example, carboxy groups in the form of an ammonium salt derived from ammonia or from a mono- or di-lower alkylamine, and also carboxy groups in the form of metal salts, for example alkali metal or alkaline earth metal salts.

Carboxy groups in anhydride form are, for example, carboxy groups in halide form, such as chlorocarbonyl, but they may also have been anhydridised by a reactive carboxylic acid and be, for example, alkoxycarbonyloxycarbonyl or trifluoroacetoxycarbonyl.

Optionally lower alkylated or lower alkanoylated amidino groups are, for example, unsubstituted or N-lower alkylated, N,N-di-lower alkylated or N-lower alkanoylated amidino groups.

The conversion of the mentioned groups X into carbamoyl that is optionally substituted as indicated is effected in customary manner, for example by solvolysis, that is to say hydrolysis or ammonolysis or aminolysis (reaction with ammonia or with a mono- or di-lower alkylamine).

By means of hydrolysis it is possible, for example, to convert unsubstituted or N-mono- or N,N-di-lower alkylated or N-lower alkanoylated amidino groups X into optionally lower alkylated or lower alkanoylated carbamoyl groups, or to convert cyano X into carbamoyl. The hydrolysis of the mentioned amidino groups is effected, for example, under acidic conditions, for example in the presence of mineral acids, for example hydrochloric or sulphuric acid. The hydrolysis of cyano is effected, for example, in the presence of a basic hydrolysis agent, such as an alkali metal hydroxide, for example in the presence of sodium hydroxide solution or potassium hydroxide solution. The hydrolysis may be facilitated by peroxy compounds, for example hydrogen peroxide, and is effected, for example, in a lower alkanol, for example ethanol, as diluent.

By means of ammonolysis or aminolysis it is possible, for example, to convert carboxy groups X that are free or esterified or in salt or anhydride form into unsubstituted or lower alkylated carbamoyl. If necessary, the operation is carried out in the presence of a condensation agent, advantageously in an inert solvent. Condensation agents are, for example, basic condensation agents, especially ammonia or the amines used for the aminolysis in excess, and when starting from carboxy that is in anhydride form they may also be alkali metal hydroxides or alkali metal carbonates, or tertiary organic nitrogen bases, such as tri-lower alkylamines or tertiary heteroaromatic nitrogen bases, for example triethylamine or pyridine. As inert solvent there is especially suitable, for example, toluene, and in the solvolysis of esterified carboxy groups, ethanol is also especially suitable. Free carboxy groups can be converted into optionally lower alkylated carbamoyl with dehydration of the ammonium salts formed intermediately, for example by heating or by the action of water-removing agents, such as acid anhydrides, for example phosphorus pentoxide, acetyl chloride and the like, or carbodiimides, for example N,N'-dicyclohexylcarbodiimide.

The starting materials of the formula III, if they are not known, can be manufactured in customary manner, for example by reacting a compound of the formula

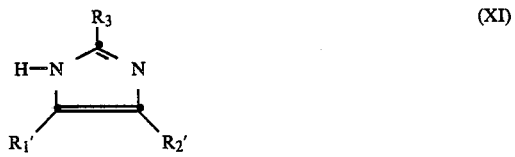

with a compound of the formula Ph—alk—$X_4$ (VI), in which $X_4$ represents reactive esterified hydroxy, for example chlorine, bromine or iodine or methane- or p-toluene-sulphonyloxy. The reaction of compounds XI and VI is effected especially in a manner analogous to that described under process variant (a). Compounds III obtainable in accordance with the process in which $R_1'$ and/or $R_2'$ represent(s) esterified carboxy or cyano can subsequently be hydrolysed, for example by treatment with sodium hydroxide or potassium hydroxide in aqueous-ethanolic solution, to form the corresponding carboxylic acids (III; $R_1'$ and/or $R_2'$=carboxy) which, in a further reaction step, can be converted into the acid chlorides (III; $R_1'$ and/or $R_2'$=chlorocarbonyl), for example by means of thionyl chloride in toluene/pyridine or phosphorus pentachloride in tetrahydrofuran, or by means of phosphorus oxychloride. Nitriles (III; $R_1'$ and/or $R_2'$=cyano) obtained initially can also be converted into the corresponding amidines (III; $R_1'$ and/or $R_2'$=optionally lower alkylated amidino) by reaction with a mineral acid, for example with hydrochloric or hydrobromic acid or sulphuric acid, and an alcohol, for example a lower alkanol or benzyl alcohol, and by further reaction of the resulting imino ether with ammonia or with a mono- or di-lower alkylamine.

According to an alternative method, compounds III are obtained by reacting a compound of the formula Ph—C(=O)—R (VIII), in which R represents hydrogen or lower alkyl, with a compound of the formula $H_2N$—C($R_1'$)=C($R_2'$)—$NH_2$ (IX), for example in the presence of sulphuric acid in boiling ethanol or tetrahydrofuran, and in the reaction product of the formula $H_2N$—C($R_1'$)=C($R_2'$)—N=C(R)—Ph (X) or $H_2N$—C($R_2'$)=C($R_1'$)—N=C(R)—Ph (IIIe) reducing the C—N double bond to the single bond, for example using sodium borohydride in methanol/tetrahydrofuran, and condensing the reaction product, for example in boiling diethylene glycol dimethyl ether, with formic acid or, in the presence of an acidic catalyst, with an orthoformic acid ester, for example at approximately from 80° to 100° C. with orthoformic acid triethyl ester. This process variant is especially suitable for the manufacture of dinitriles (III; $R_1'$=$R_2'$=cyano), which, if desired, can be hydrolysed as described above to form the dicarboxylic acid (III; $R_1'$=$R_2'$=carboxy) and, if desired, subsequently esterified or anhydridised or converted into a corresponding bis-amidine III, in which $R_1'$ and $R_2'$ each represents an optionally N-mono- or N,N-di-lower alkylated amidino group.

In starting materials V for process variant (c), nucleophilic leaving groups $X_3$ are, for example, disubstituted amino groups, such as di-lower alkylamino, for example dimethylamino, or 5- to 7-membered alkyleneamino, for example pyrrolidino or piperidino, or aza-, oxa- or thia-alkyleneamino, for example N'-methylpiperazino, morpholino or thiomorpholino.

The reaction of compounds IV and V is effected in customary manner, for example by heating in an inert solvent, such as an aromatic or araliphatic hydrocarbon, for example benzene, toluene or xylene, in a temperature range of approximately from 80° to 180° C., preferably of approximately from 110° to 150° C.

Starting materials IV can be manufactured, for example, by reacting compounds of the formula Ph—alk—$X_4$ (VI; $X_4$=chlorine, bromine or iodine) with ammonia under basic conditions or by the reduction of corresponding nitriles of the formula Ph—CN (XIII), for example by means of a bi-light metal hydride, for example by means of lithium aluminium hydride.

Starting materials V are obtained, for example, by converting a 2-isocyanoacetic acid lower alkyl ester, by treatment with a di-lower alkylamine, into the corresponding 2-isocyano-N,N-di-lower alkylacetamide and reacting the latter with an N,N-disubstituted formamide acetal, for example with an N,N-di-lower alkyl-, 5- to 7-membered N,N-alkylene- or N,N-aza-, N,N-oxa- or N,N-thia-alkylene-formamide di-lower alkyl acetal, for example with N,N-dimethylformamide dimethyl acetal.

In accordance with a particularly elegant process for the manufacture of compounds I in which $R_1$ represents hydrogen or lower alkyl and $R_3$ represents hydrogen, a compound of the formula Ph—alk—$NH_2$ (IV) is reacted in an inert solvent with a corresponding isonitrile of the formula CN—C($R_2'$)=CH—$X_3$ (XII), in which $R_2'$ represents N,N-di-lower alkylcarbamoyl or esterified carboxy, to form a compound I in which $R_1$ represents hydrogen or lower alkyl, $R_2$ represents N,N-di-lower alkyl and $R_3$ represents hydrogen, or to form a compound III in which $R_1'$ represents hydrogen or lower alkyl, $R_2'$ represents esterified carboxy and $R_3$ represents hydrogen. The latter compound is then converted into the corresponding compound I, in which $R_2$ is carbamoyl or N-lower alkylcarbamoyl, by reaction with ammonia or with a lower alkylamine in accordance with process variant (b). Suitable nucleofugal leaving groups are, for example, dimethylamino, or 5- to 7-membered alkyleneamino, for example pyrrolidino or piperidino, or aza-, oxa- or thia-alkyleneamino, for example N'-methylpiperazino, morpholino or thiomorpholino, as indicated for process variant (c). The operation is preferably carried out while heating, for example in a temperature range of approximately from 80° to 180° C., for example at boiling temperature.

Compounds obtainable in accordance with the process can be converted into different compounds of the formula I by converting one or more variables in the general formula I into others.

For example, it is possible to convert unsubstituted carbamoyl $R_2$ and, where appropriate, $R_1$ into N-mono- or N,N-di-lower alkylcarbamoyl and to convert N-mono-lower alkylcarbamoyl $R_2$ and, where appropriate, $R_1$ into N,N-di-lower alkylcarbamoyl, for example by treatment with a reactive ester of a lower alkanol, such as a lower alkyl halide, for example a lower alkyl bromide or iodide, a lower alkylsulphonate, for example methanesulphonate or p-toluenesulphonate, or a di-lower alkyl sulphate, for example dimethyl sulphate, preferably under basic conditions, such as in the presence of sodium amide or sodium hydride or in the presence of sodium hydroxide solution or potassium hydroxide solution and a phase transfer catalyst, such as tetrabutylammonium bromide or benzyltrimethylammonium chloride. In analogous manner it is also possible to convert carbamoyl $R_2$ and/or $R_1$ into N-lower alkanoylcarbamoyl, but more strongly basic condensation agents, such as alkali metal amides or alkali metal alcoholates, for example sodium amide or sodium methoxide, may be necessary.

Depending on the number of asymmetric carbon atoms, the novel compound can be in the form of a pure optical isomer (enantiomer or diastereoisomer) or in the form of mixtures thereof (racemates, diastereoisomeric mixtures or mixtures of racemates).

Resulting isomeric mixtures of imidazole-4(5)-carboxamides and their derivatives that are lower alk(ano)ylated at the amido group, and also diastereoisomeric mixtures and mixtures of racemates that are obtainable in accordance with the process can be separated in known manner into the pure position isomers, diastereoisomers or racemates on the basis of the physico-chemical differences between the components, for example by chromatography and/or fractional crystallisation. Resulting diastereoisomeric mixtures, for example racemates, can also be resolved into the optical antipodes by known methods, for example by recrystallisation from an optically active solvent, with the aid of microorganisms or by reacting an acidic precursor, for example of the formula III (X=carboxy), with an optically active base that forms salts with the acid of the racemate, and separating the diastereoisomeric salts thus obtained, for example on the basis of their different solubilities, into the diastereoisomers, from which the antipodes can be freed by the action of suitable agents. Suitable optically active bases are, for example, corresponding alkaloids, such as brucine, strychnine, ephedrine, quinine, quinidine or andronine, and also menthylamine or α-phenylethylamine.

The invention also relates to those forms of the process according to which a compound obtainable as an intermediate at any stage of the process is used as starting material and the remaining steps are carried out, or a starting material is used in the form of a salt, or, especially, is formed under the reaction conditions.

The invention also relates to novel starting materials which have been developed specifically for the manufacture of the compounds according to the invention, especially the group of starting materials resulting in the compounds of the formula I characterised at the beginning as being preferred, to the processes for their manufacture and to their use as intermediates.

The novel compounds of the formula I can be used, for example, in the form of pharmaceutical preparations which contain a therapeutically effective amount of the active ingredient, optionally together with inorganic or organic, solid or liquid pharmaceutically acceptable carriers that are suitable for enteral, for example oral, or parenteral administration. For example, there are used tablets or gelatine capsules which contain the active ingredient together with diluents, for example lactose, dextrose, saccharose, mannitol, sorbitol, cellulose and/or glycine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat, rice or arrowroot starch, gelatine, tragacanth, methylcellulose, sodium carboxymethylcellulose, and/or polyvinylpyrrolidone, and, if desired, disintegrators, for example starches, agar, alginic acid or a salt thereof, such as sodium alginate, and/or effervescent mixtures, or adsorbents, colourings, flavourings and sweeteners. The novel compound of the formula I can also be used in the form of preparations that can be administered parenterally, or as infusion solutions. Such solutions are preferably isotonic aqueous solutions or suspensions which, for example in the case of lyophilised preparations containing the active ingredient alone or together with a carrier, for example mannitol, may be prepared before use. The pharmaceutical preparations may be sterilised and/or may contain adjuncts, for example preservatives, stabilisers, wetting agents and/or emulsifiers, solubilisers, salts for regulating the osmotic pressure and/or buffers. The present pharmaceutical preparations which, if desired, may contain further pharmacologically active substances, are manufactured in a manner which is known per se, for example by means of conventional mixing, granulating, confectioning, dissolving or lyophilising processes, and contain from approximately 0.1% to 100%, especially from approximately 1% to 50%, in the case of lyophilisates up to 100%, of the active ingredient.

The invention likewise relates to the use of the compounds of the formula I, preferably in the form of pharmaceutical preparations. The dosage can depend on various factors, such as the mode of administration, species, age and/or individual condition. In the case of oral administration, the doses to be administered daily are between approximately 5 and approximately 50 mg/kg and for warm-blooded animals weighing approximately 70 kg they are preferably between approximately 0.5 g and approximately 5.0 g.

The following Examples serve to illustrate the invention; temperatures are given in degrees Celsius.

EXAMPLE 1

5.34 g of 1-(2,3-difluorobenzyl)-imidazole-4-carboxylic acid ethyl ester are dissolved in 80 ml of methanol and transferred to an autoclave. 20.0 g of ammonia are introduced under pressure and the whole is heated at 100° for 19 hours. When the excess ammonia has been blown off, the resulting product is filtered off and recrystallised from ethanol. 1-(2,3-difluorobenzyl)-imidazole-4-carboxamide having a melting point of 221°-222° is obtained.

The following are obtained analogously:

1-(2,4-difluorobenzyl)-imidazole-4-carboxamide, m.p. 220°–221°;
1-(2,5-difluorobenzyl)-imidazole-4-carboxamide, m.p. 214°–215° (from dioxan);
1-(2,6-difluorobenzyl)-imidazole-4-carboxamide, m.p. 227°–229° (from ethanol);
1-(2,3-difluorobenzyl)-imidazole-5-carboxamide, m.p. 199°–200° (from isopropanol);
1-(2,4-difluorobenzyl)-imidazole-5-carboxamide, m.p. 207°–208° (from isopropanol);
1-(2,5-difluorobenzyl)-imidazole-5-carboxamide, m.p. 211°–212° (from isopropanol);
1-(2,6-difluorobenzyl)-imidazole-5-carboxamide, m.p. 184°–185° (from methanol);
1-(2,6-difluorobenzyl)-imidazole-4,5-dicarboxamide, m.p. 218°–220° (from dioxan/ether);
1-(o-chlorobenzyl)-imidazole-4,5-dicarboxamide, m.p. 237°–238° (from acetic acid/water);
1-(o-methylbenzyl)-imidazole-4,5-dicarboxamide, m.p. 219°–221° (from dioxan);
1-(2,6-difluorobenzyl)-2-methylimidazole-4,5-dicarboxamide, m.p. above 300° (from acetic acid/water);
1-(2,6-difluorobenzyl)-4-methylimidazole-5-carboxamide, m.p. 233°–235°;
1-(o-chlorobenzyl)-4-methylimidazole-5-carboxamide, m.p. 252°–254°;
1-(2,6-difluorobenzyl)-5-methylimidazole-4-carboxamide, m.p. 235°–236°;
1-(o-chlorobenzyl)-5-methylimidazole-4-carboxamide, m.p. 193°–195°;
1-(2,6-difluorobenzyl)-2-methyl-4-carboxamide, m.p. 266°–267°;
1-[1-(2,6-difluorophenyl)-ethyl]-imidazole-4-carboxamide, m.p. 220°, and
1-[1-(2,6-difluorophenyl)-ethyl]-imidazole-5-carboxamide, m.p. 163°–165°.

The starting materials can be manufactured, for example, as follows:

(a) 1.32 g of sodium are dissolved in 150 ml of ethanol. 6.72 g of imidazole-4-carboxylic acid ethyl ester and 9.9 g of 2,3-difluorobenzyl bromide are added and the whole is heated under reflux for 3.5 hours while stirring. The reaction mixture is concentrated by evaporation under reduced pressure and the residue is stirred with ice-water and extracted by shaking three times with 50 ml of ethyl acetate each time. The extracts are combined, washed with water and with saturated sodium chloride solution, dried over magnesium sulphate and concentrated to dryness by evaporation under reduced pressure. 1-(2,3-difluorobenzyl)-imidazole-4(5)-carboxylic acid ethyl ester is obtained in the form of an isomeric mixture which can be separated into the components, 1-(2,3-difluorobenzyl)-imidazole-4-carboxylic acid ethyl ester, m.p. 95°–100° (from toluene/hexane) and 1-(2,3-difluorobenzyl)-imidazole-5-carboxylic acid ethyl ester (oil), by chromatography on silica gel as the stationary phase and toluene/isopropanol (9:1) as the mobile phase. (b) 13.0 g of 2,6-difluorobenzyl alcohol and 8.4 g of methanesulphonyl chloride are dissolved in 90 ml of methylene chloride, and 17.6 ml of triethylamine in 18 ml of methylene chloride are added dropwise while stirring in an ice bath. The rate at which the triethylamine is added is so regulated that the internal temperature does not exceed 10°. The whole is stirred for a further 40 minutes in the ice bath and then 90 ml of ice-water are added and the whole is stirred for a further 60 minutes. The organic phase is separated off and dried over magnesium sulphate, and 21 g of the monosodium salt of imidazole-4,5-dicarboxylic acid diethyl ester (obtainable, for example, by reacting imidazole-4,5-dicarboxylic acid diethyl ester with 2.53 g of sodium dissolved in 60 ml of ethanol) are added. The whole is stirred for 3 hours at room temperature, washed three times with water, dried over magnesium sulphate, concentrated to dryness by evaporation, dissolved in toluene/ethyl acetate (1:1), filtered over silica gel, again concentrated to dryness by evaporation and recrystallised from ether/petroleum ether. 1-(2,6-difluorobenzyl)-imidazole-4,5-dicarboxylic acid diethyl ester having a melting point of 68°–70° is obtained.

The following are obtained analogously:

1-(2,4-difluorobenzyl)-imidazole-4-carboxylic acid ethyl ester, m.p. 89°–90°, and 1-(2,4-difluorobenzyl)-imidazole-5-carboxylic acid ethyl ester, m.p. 70°–72°;
1-(2,5-difluorobenzyl)-imidazole-4-carboxylic acid ethyl ester, m.p. 138°–139°, and 1-(2,5-difluorobenzyl)-imidazole-5-carboxylic acid ethyl ester, m.p. 74°–75°;
1-(2,6-difluorobenzyl)-imidazole-4-carboxylic acid ethyl ester, m.p. 114°–115°, and 1-(2,6-difluorobenzyl)-imidazole-5-carboxylic acid ethyl ester, m.p. 63°–64°;

and also, starting from 4-methylimidazole-5-carboxylic acid ethyl ester, 1-(2,6-difluorobenzyl)-4-methylimidazole-5-carboxylic acid ethyl ester, m.p. 59°–61° (from hexane) and 1-(2,6-difluorobenzyl)-5-methylimidazole-4-carboxylic acid ethyl ester, m.p. 107°–108° (from toluene/ether), 1-(o-chlorobenzyl)-4-methylimidazole-5-carboxylic acid ethyl ester, m.p. 74°–76°, and 1-(o-chlorobenzyl)-5-methylimidazole-4-carboxylic acid ethyl ester, m.p. 100°–104°; and also, starting from imidazole-4,5-dicarboxylic acid diethyl ester, 1-(2,6-difluorobenzyl)-imidazole-4,5-dicarboxylic acid diethyl ester, m.p. 71°–73° (from petroleum ether), 1-(o-chlorobenzyl)-imidazole-4,5-dicarboxylic acid diethyl ester, m.p. 69°–70° (from ether/hexane) and 1-(o-methylbenzyl)-imidazole-4,5-dicarboxylic acid diethyl ester (oil); and also, starting from 2-methylimidazole-4,5-dicarboxylic acid diethyl ester, 1-(2,6-difluorobenzyl)-2-methylimidazole-4,5-dicarboxylic acid diethyl ester, m.p. 63°–64° (from ether/hexane).

(c) 16.37 g of 1-(2,6-difluorophenyl)-ethanol are dissolved in 74 ml of hexane; 74 ml of 48% hydrobromic acid are added and the whole is heated under reflux for 90 minutes, while stirring. The whole is allowed to cool, the organic phase is separated off and the aqueous phase is extracted by shaking three times with hexane. The combined hexane phases are dried over magnesium sulphate and filtered. The resulting solution of 1-(2,6-difluorophenyl)-ethyl bromide is added to a solution of 14.5 g of imidazole-4(5)-carboxylic acid ethyl ester in 100 ml of ethanol, to which a solution of 2.39 g of sodium in 50 ml of ethanol has previously been added. The hexane is distilled off and then the reaction mixture is heated for 3 hours under reflux. After working up analogously to 1a), 1-[1-(2,6-difluorophenyl)-ethyl]-imidazole-4-carboxylic acid ethyl ester, m.p. 96°–97°, and 1-[1-(2,6-difluorophenyl)-ethyl]-imidazole-5-carboxylic acid ethyl ester, m.p. 106°–107°, are obtained.

EXAMPLE 2

By reacting 1-(2,6-difluorobenzyl)-imidazole-4-carboxylic acid ethyl ester with the corresponding amount of methylamine or dimethylamine in a manner analogous to that described in Example 1, 1-(2,6-difluorobenzyl)-imidazole-4-(N-methyl)-carboxamide, m.p. 155°–157° (from ethyl acetate), and 1-(2,6-difluorobenzyl)-imidazole-4-(N,N-dimethyl)-carboxamide, m.p. 113°–115° (from ethyl acetate/hexane), are obtained, and by reacting 1-(2,6-difluorobenzyl)-imidazole-4-carboxylic acid ethyl ester with the corresponding amount of ethylamine, 1-(2,6-difluorobenzyl)-imidazole-4-(N-ethyl)-carboxamide, m.p. 112°–114°, is obtained, and by reacting 1-(2,6-difluorobenzyl)-imidazole-5-carboxylic acid ethyl ester with methylamine, 1-(2,6-difluorobenzyl)-imidazole-5-(N-methyl)-carboxamide, m.p. 128°–130°, is obtained.

EXAMPLE 3

4.0 g of 1-(o-fluorobenzyl)-imidazole-4-carboxylic acid methyl ester are dissolved in 80 ml of methanol and transferred to an autoclave. 20.0 g of ammonia are introduced under pressure and the whole is heated at 100° for 19 hours. When the excess ammonia has been blown off, the resulting product is filtered off and recrystallised from ethanol. 1-(o-fluorobenzyl)-imidazole-4-carboxamide having a melting point of 204°–205° is obtained.

The following are obtained analogously:
1-(2,6-difluorobenzyl)-imidazole-4-carboxamide, m.p. 227°–229° (methanol);
1-(o-chlorobenzyl)-imidazole-4-carboxamide, m.p. 238°–239°;
1-(o-methylbenzyl)-imidazole-4-carboxamide, m.p. 245°–245.5°, and
1-(3,4-difluorobenzyl)-imidazole-4-carboxamide, m.p. 184°–185°.

The starting materials may be manufactured, for example, as follows:

8 g of o-fluorobenzylamine and 6.6 g of 2-isocyano-3-dimethylaminoacrylic acid methyl ester are dissolved in 66 ml of xylene and heated under reflux for 3 hours while stirring. After cooling to room temperature, the whole is diluted with ethyl acetate and extracted by shaking twice with 50 ml of 2N hydrochloric acid each time and then with water. The aqueous phases are washed twice with 50 ml of ethyl acetate each time. All the aqueous phases are combined, rendered alkaline with concentrated ammonia and then extracted by shaking three times with 100 ml of dichloromethane each time. The extracts are combined, washed twice with water, dried over magnesium sulphate and concentrated to dryness by evaporation. The residue is dissolved in ethyl acetate, filtered over silica gel, concentrated and caused to crystallise by the addition of diethyl ether. 1-(o-fluorobenzyl)-imidazole-4-carboxylic acid methyl ester having a melting point of 87°–89° is obtained.

The following are obtained analogously:
1-(2,6-difluorobenzyl)-imidazole-4-carboxylic acid methyl ester, m.p. 107°–109°;
1-(o-chlorobenzyl)-imidazole-4-carboxylic acid methyl ester, m.p. 82°–83°;
1-(o-methylbenzyl)-imidazole-4-carboxylic acid methyl ester, m.p. 89°–90°, and
1-(3,4-difluorobenzyl)-imidazole-4-carboxylic acid methyl ester, m.p. 139°–141° C.

EXAMPLE 4

15.7 g of 2,6-difluorobenzylamine and 11.2 g of 2-isocyano-3-dimethylaminoacrylic acid (N,N-dimethyl)amide are dissolved in 150 ml of toluene and heated under reflux for 3 hours while stirring. After cooling to room temperature, the whole is diluted with ethyl acetate and extracted by shaking twice with 50 ml of 2N hydrochloric acid each time and then with water. The aqueous phases are washed twice with 50 ml of ethyl acetate each time. All the aqueous phases are combined, rendered alkaline with ammonia and extracted by shaking three times with 100 ml of trichloromethane (chloroform) each time. The extracts are combined, washed twice with water, dried over magnesium sulphate and concentrated to dryness by evaporation. The residue is dissolved in ethyl acetate, filtered over silica gel, concentrated and caused to crystallise by the addition of diethyl ether. 1-(2,6-difluorobenzyl)-imidazole-4-(N,N-dimethyl)-carboxamide having a melting point of 113°–115° (from ether/hexane) is obtained.

EXAMPLE 5

0.29 g of sodium are dissolved in 30 ml of ethanol. 1.9 g of imidazole-4,5-di(N-methyl)carboxamide and 2.4 g of 2,6-difluorobenzyl bromide are added and the whole is heated under reflux for 5 hours, while stirring. The reaction mixture is concentrated to dryness by evaporation and the residue is taken up in methylene chloride, extracted by shaking with water, dried over magnesium sulphate and concentrated by evaporation. The residue is dissolved in toluene/ethyl acetate (1:1), filtered over silica gel, again concentrated by evaporation and recrystallised from ethyl acetate. 1-(2,6-difluorobenzyl)-imidazole-4,5-di(N-methyl)carboxamide having a melting point of 112°–113° is obtained. 1-(2,6-difluorobenzyl)-imidazole-4,5-di(N,N-dimethyl)carboxamide having a melting point of 184°–185° is also obtained analogously.

The starting materials can be manufactured, for example, as follows:

6.36 g of imidazole-4,5-dicarboxylic acid ethyl ester are dissolved in 140 ml of ethanol and transferred to an autoclave. 45 g of dimethylamine are introduced under pressure and the whole is heated at 100° for 45 hours and at 110° for 30 hours. The reaction mixture is concentrated to dryness by evaporation, purified by chromatography on silica gel with ethyl acetate/methanol (2:1) and crystallised from ethyl acetate. Imidazole-4,5-di(N,N-dimethyl)-carboxamide having a melting point of 108°–110° is obtained; imidazole-4,5-di(N-methyl)-carboxamide is also obtained analogously using methylamine.

EXAMPLE 6

76 mg of sodium are dissolved in 3 ml of ethanol. 333 mg of imidazole-4-carboxamide are added and the whole is stirred for 30 minutes at room temperature. 64 mg of 2,6-difluorobenzyl bromide dissolved in 2 ml of ethanol are added and the whole is stirred for a further 3 hours at room temperature. The reaction mixture is concentrated to dryness by evaporation. A mixture of 1-(2,6-difluorobenzyl)-imidazole-4-and -5-carboxamide is obtained, which can be separated into the components, 1-(2,6-difluorobenzyl)-imidazole-4-carboxamide, m.p. 227°–229° (from ethanol), and 1-(2,6-difluorobenzyl)-imidazole-5-carboxamide, m.p. 184°–185° (from methanol), by chromatography on silica gel with ethyl acetate/isopropanol (7:2) as eluant.

EXAMPLE 7

10.1 g of 1-(2,6-difluorobenzyl)-imidazole-4-carboxamide are introduced in portions into a mixture, heated to 60°, of 30.7 g of acetic anhydride and 0.1 ml of sulphuric acid, while stirring. Stirring is continued for a further 30 minutes at 60°–70° and then the whole is poured into 250 ml of ethanol, heated under reflux for 30 minutes, concentrated to dryness by evaporation under reduced pressure and digested with 250 ml of ethyl acetate. The crystalline precipitate that forms directly is filtered off with suction and recrystallised from ethyl acetate. 1-(2,6-difluorobenzyl)-imidazole-4-(N-acetyl)-carboxamide is obtained.

EXAMPLE 8

To a solution of 10.0 g of 1-(o-methylbenzyl)-imidazole-4,5-dinitrile in 300 ml of ethanol and 25 ml of 5N sodium hydroxide solution there are added dropwise at 40°–50° 25 ml of 30% hydrogen peroxide solution. The whole is stirred at 40°–50° for 2 hours, diluted with 500 ml of water and filtered with suction. After washing with water and recrystallisation from dioxan, 1-(o-methylbenzyl)-imidazole-4,5-dicarboxamide having a melting point of 219°–221° is obtained.

The starting material can be manufactured, for example, as follows:

3.70 g of sodium are dissolved in 375 ml of ethanol and then 14.6 g of imidazole-4,5-dinitrile and 16.5 ml of o-methylbenzyl chloride are added and the whole is heated under reflux for 8 hours. The whole is concentrated to dryness by evaporation under reduced pressure and the residue is taken up in dichloromethane, washed in succession with water and with saturated sodium chloride solution, dried over sodium sulphate and concentrated to dryness by evaporation. The crude product is purified by chromatography on silica gel with toluene/ethyl acetate (5:1) and crystallised from ethyl acetate/hexane. 1-(o-methylbenzyl)-imidazole-4,5-dinitrile having a melting point of 80°–81° is obtained.

EXAMPLE 9

The following are also obtained in a manner analogous to that described in Examples 1 to 8:
1-(2,6-difluorobenzyl)-imidazole-5-(N-acetyl)-carboxamide;
1-(2,6-difluorobenzyl)-imidazole-4,5-di(N-acetyl)carboxamide.

EXAMPLE 10

Tablets each containing 50 mg of 1-(2,6-difluorobenzyl)-imidazole-4-carboxamide can be manufactured as follows:

| Composition (10,000 tablets) | |
| --- | --- |
| Active ingredient | 500.0 g |
| Lactose | 500.0 g |
| Potato starch | 352.0 g |
| Gelatine | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch and the mixture is moistened with an alcoholic solution of the gelatine and granulated through a sieve. After drying, the remainder of the potato starch, the talc, the magnesium stearate and the highly disperse silica are mixed in and the mixture is compressed to form tablets which each weight 145.0 mg and contain 50.0 mg of active ingredient and which, if desired, can be provided with dividing notches for finer adjustment of the dosage.

EXAMPLE 11

Lacquer-coated tablets each containing 100 mg of 1-(2,6-difluorobenzyl)-imidazole-4-carboxamide can be manufactured as follows:

| Composition (10,000 tablets) | |
| --- | --- |
| Active ingredient | 100.00 g |
| Lactose | 100.00 g |
| Corn starch | 70.00 g |
| Talc | 8.50 g |
| Calcium stearate | 1.50 g |
| Hydroxypropylmethylcellulose | 2.36 g |
| Shellac | 0.64 g |
| Water | q.s. |
| Methylene chloride | q.s. |

The active ingredient, the lactose and 40 g of the corn starch are mixed and moistened with a paste prepared from 15 g of corn starch and water (while heating), and granulated. The granulate is dried and the remaining corn starch, the talc and the calcium stearate are added and mixed with the granulate. The mixture is compressed to form tablets (weight: 280 mg) and these are coated with a solution of the hydroxypropylmethycellulose and the shellac in methylene chloride; final weight of the lacquer-coated tablets: 283 mg.

EXAMPLE 12

In a manner analogous to that described in Examples 10 and 11 it is also possible to manufacture tablets or lacquer-coated tablets containing a different compound according to Examples 1 to 9.

I claim:
1. Novel 1-phenyl-lower alkylimidazole-4- or 5-carboxamides of the formula

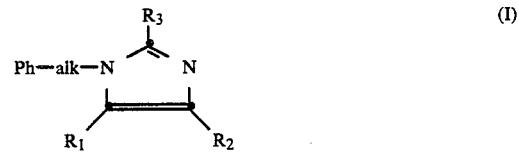

in which Ph denotes o-$C_1$–$C_4$-alkylphenyl, o-halophenyl or 2,6-dihalophenyl, alk represents methylene, and wherein $R_1$ denotes hydrogen and $R_2$ denotes carbamoyl, N-$C_1$–$C_4$-alkylcarbamoyl or N,N-di-$C_1$–$C_4$-alkylcarbamoyl or, if Ph denotes 2,6-dihalophenyl, $R_1$ denotes carbamoyl, N-$C_1$–$C_4$-alkylcarbamoyl or N,N-di-$C_1$–$C_4$-alkylcarbamoyl and $R_2$ and $R_3$ denote hydrogen.

2. A pharmaceutical composition comprising an antiepileptically effective amount of a compound of the formula

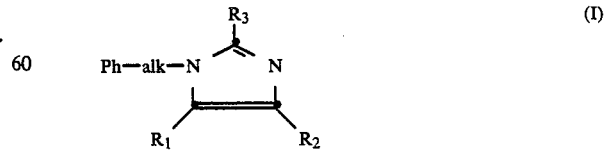

in which Ph denotes o-$C_1$–$C_4$-alkylphenyl, o-halophenyl or 2,6-dihalophenyl, alk represents methylene, and wherein $R_1$ denotes hydrogen and $R_2$ denotes carbamoyl, N-$C_1$–$C_4$-alkylcarbamoyl or N,N-di-$C_1$–$C_4$-alkylcarbamoyl or, if Ph denotes 2,6-di-halophenyl, $R_1$ denotes carbamoyl, N-$C_1$-$C_4$-alkylcarbamoyl or N,N-di-$C_1$-$C_4$-alkylcarbamoyl and $R_2$ and $R_3$ denote hydrogen and a pharmaceutically acceptable carrier.

3. A compound according to claim 1, in which Ph represents o-$C_1$-$C_4$-alkylphenyl, o-halophenyl or 2,6-dihalophenyl, alk represents methylene, $R_1$ represents hydrogen, $R_2$ represents carbamoyl, N-$C_1$-$C_4$-alkylcarbamoyl, N,N-di-$C_2$-$C_4$-alkylcarbamoyl or N-$C_2$-$C_4$-alkanoylcarbamoyl, and $R_3$ represents hydrogen.

4. A compound according to claim 1, in which Ph represents o-$C_1$-$C_4$-alkylphenyl, o-halophenyl or 2,6-dihalophenyl, alk represents methylene, $R_1$ represents hydrogen, $R_2$ represents carbamoyl and $R_3$ represents hydrogen.

5. A compound as claimed in claim 1, being 1-(2,6-difluorobenzyl)-imidazole-4-carboxamide.

6. A compound as claimed in claim 1, being 1-(o-chlorobenzyl)-imidazol-4-carboxamide.

7. A compound as claimed in claim 1 being 1-(2,6-difluorobenzyl)-imidazole-4-(N-methyl-carboxamide.

8. A compound as claimed in claim 1 being 1-(o-fluorobenzyl)-imidazole-4-carboxamide.

9. A compound as claimed in claim 1 being 1(2,6-difluorobenzyl)-imidazole-4-(N,N-dimethyl)-carboxamide.

10. A compound as claimed in claim 1 being 1-(2,6-difluorobenzyl)-2-methyl-4-carboxamide.

11. A compound as claimed in claim 1 being 1-(o-methylbenzyl)-imidazole-4-carboxamide.

12. A compound as claimed in claim 1 being 1-(2,6-difluorobenzyl)-imidazole-4-(N-ethyl)-carboxamide.

13. A method for the preventive or ameliorating treatment of seizures or convulsions associated with epilepsy in a host in need thereof comprising administering to said host a therapeutically effective amount of a compound of the formula

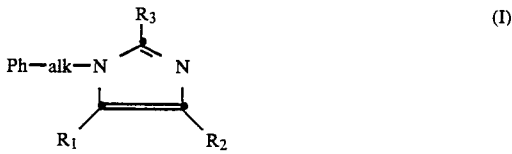

wherein
Ph is phenyl which is mono, di or tri substituted by substituents selected from lower alkyl and halogen;
alk is lower alkylidene; one of $R_1$ and $R_2$ is selected from carbamoyl,
N-lower alkylcarbamoyl, N,N-di-lower alkylcarbamoyl, and N-lower alkanoylcarbamoyl;
and the other of $R_1$ and $R_2$ is selected from hydrogen, lower alkyl, carbamoyl, N-lower alkylcarbamoyl, N,N-di-lower alkylcarbamoyl, and N-lower alkanoylcarbamoyl; and $R_3$ is hydrogen or lower alkyl.

* * * * *